United States Patent
Alonso (12)

(10) Patent No.: US 6,686,191 B1
(45) Date of Patent: Feb. 3, 2004

(54) PREPARATION OF VIRALLY INACTIVATED INTRAVENOUSLY INJECTABLE IMMUNE SERUM GLOBULIN

(75) Inventor: William R. Alonso, Cary, NC (US)

(73) Assignee: Bayer HealthCare LLC, Tarrytown, NY (US)

( * ) Notice: Subject to any disclaimer, the term of this patent is extended or adjusted under 35 U.S.C. 154(b) by 1772 days.

(21) Appl. No.: 08/532,211

(22) Filed: Sep. 22, 1995

(51) Int. Cl.[7] .................. C12N 7/04; A61K 39/395; A61K 39/40; A61K 39/42

(52) U.S. Cl. ................. 435/236; 424/176.1; 424/177.1; 424/130.1

(58) Field of Search .................. 530/390.1, 390.5, 530/386, 387.1; 424/176.1, 177.1, 130.1; 435/236

(56) References Cited

U.S. PATENT DOCUMENTS 4,396,608 A * 8/1983 Tenold
4,540,573 A * 9/1985 Neurath et al.
4,762,714 A * 8/1988 Mitra et al.

OTHER PUBLICATIONS

Joy Yang, Y.H. et al. "Antibody Fc functional activity of intravenous immunoglobulin preparations treated with solvent–detergent for virus inactivation" Vox Sang, vol. 67, pp. 337–344, May 17, 1994).*

* cited by examiner

*Primary Examiner*—Yvonne Eyler
(74) *Attorney, Agent, or Firm*—Connolly Bove Lodge & Hutz LLP

(57) ABSTRACT

Method of reducing the anticomplement activity (ACA) resulting from viral inactivation treatment of a solution of antibodies, the method comprising contacting the solution with a trialkylphosphate, such as tri-n-butyl phosphate, and a detergent, such as sodium cholate, under conditions sufficient to reduce substantially the virus activity, and then incubating the solution under controlled conditions of time, pH, temperature, and ionic strength such that the anticomplement activity is reduced to an acceptable level. In a preferred embodiment, the ACA is reduced to less than 60 $CH_{50}$ units/mL, the incubation is for at least about ten days at a pH from 3.5 to 5.0, the temperature is maintained within a range of 2 to 50° C., and the ionic strength of the solution is less than about 0.001 M.

24 Claims, 1 Drawing Sheet

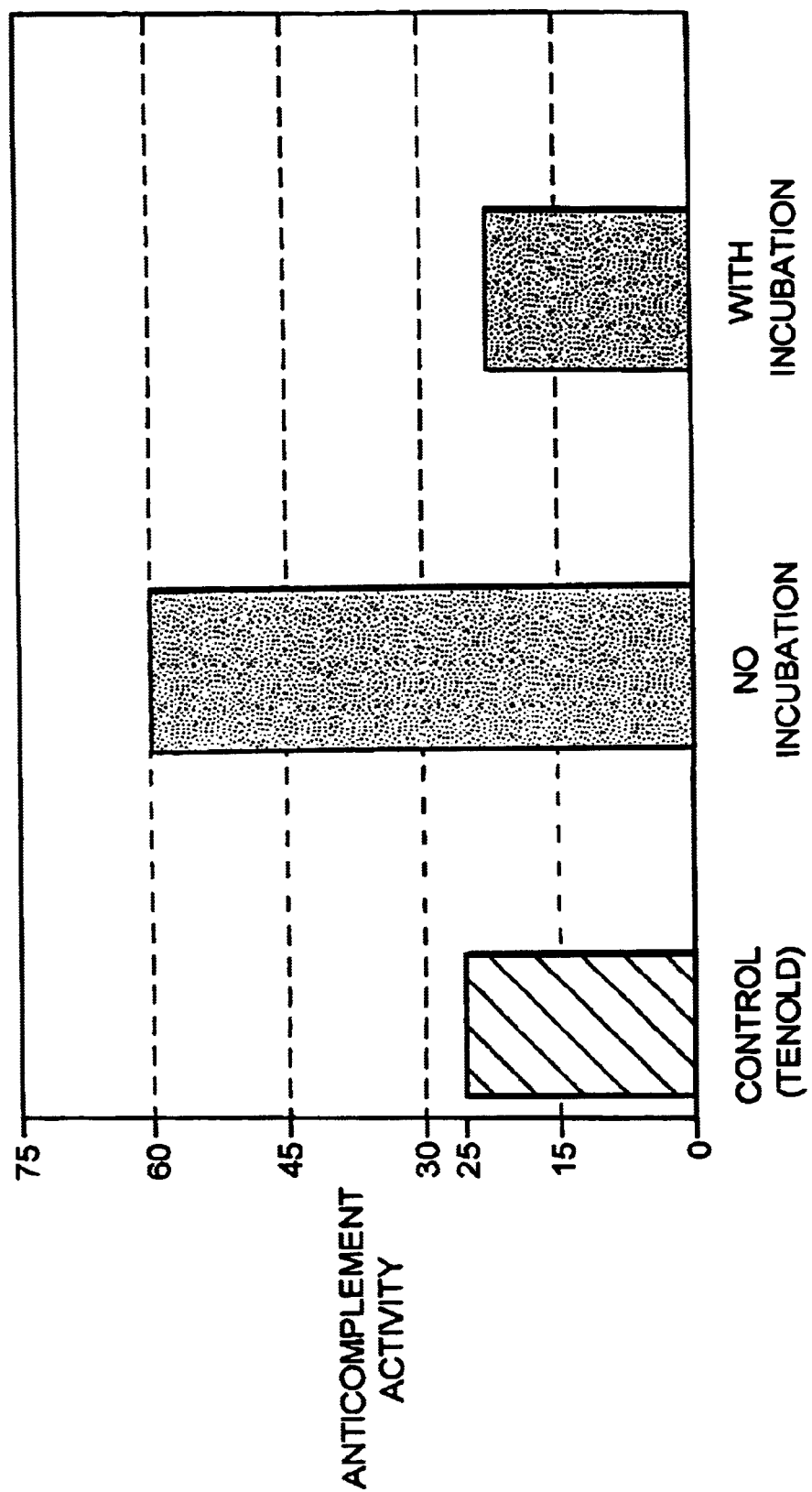

PREPARATION OF VIRALLY INACTIVATED INTRAVENOUSLY INJECTABLE IMMUNE SERUM GLOBULIN

BACKGROUND OF THE INVENTION

1. Field

This invention generally deals with an intravenously injectable immunoglobulin product, and more specifically deals with an intravenously injectable immune serum globulin (IGIV) which has been subjected to a virus inactivation step and which has a low level of anticomplement activity.

2. Background

Early pharmaceutical preparations of immune serum globulins could not be administered intravenously due to an unacceptably high incidence of adverse reactions. These adverse reactions were associated with a decrease in serum complement levels, apparently caused by complement binding to the administered gamma globulin. (1) The ability of gamma globulin to bind complement, or its anticomplement activity (ACA), is greatly increased as a result of denaturation brought about during the fractionation procedure. Several approaches have been taken to address the problem of rendering ISG safe for intravenous administration. (See (2) and references therein). Tenold reported a method of preparing an immune serum globulin (ISG) with low ACA which could be administered by intravenous injection. (2, incorporated herein by reference). The Tenold '608 process requires formulating the ISG at low ionic strength (preferably less than about 0.001) and at low pH (3.5–5.0).

Other methods of preparing intravenously injectable immune serum globulin (IGIV) have been reported, including stabilizing with carbohydrates such as maltose (3). A process including incubation of ISG at pH 4.0 at 37° C. (4) results in a product with low ACA which may be administered by intravenous injection; however, upon storage the product regains its high ACA. IGIV has also been prepared by covalent modification of the ISG, for example by proteolysis (5) or by reduction of disulfide linkages followed by reaction with a blocking agent (1,6).

Antibody preparations, since they are isolated blood products, have an inherent hazard of transmitting virally-mediated diseases. Inactivation of viruses is an important step in producing safe and effective blood products. U.S. Pat. No. 4,540,573 to Neurath et al., which is incorporated herein by reference, describes a viral inactivation process using a trialkyl phosphate and detergent process (hereinafter, the solvent/detergent process, or SD process). (7) That solvent/detergent method has gained acceptance as being efficacious in the inactivation of lipid-enveloped viruses with limited adverse effects on biological activity or blood product profile. (8, 15; See also 12 for a discussion of various viral inactivation processes).

Current antibody preparations on the market generally have been regarded as safe with respect to viral contamination. (9) This is thought to be due to features of the fractionation processes used to isolate these blood products. However, it would be desirable to further ensure the safety of the antibody preparations by including a distinct viral inactivation step in the production process. Successful reduction of viral activity in an IGIV solution was reported using several different methods of viral inactivation for a variety of viruses. (16, 17) A process for preparation of immunoglobulins substantially free of retrovirus has been reported involving incubation of ISG under controlled conditions of time, temperature, and pH. The process entails isolating ISG via a cold ethanol plasma fractionation process and then storage of the ISG at one of two storage conditions: (a) at pH≦4.25 at a temperature of 27° C. for at least three days, or (b) at pH≦6.8 at a temperature of 45° C. for at least six hours. (10).

We have found that using the SD process to treat ISG preparations, especially those subsequently formulated according to the Tenold '608 patent, results in a product with an acceptable viral inactivation but with unacceptably high levels of ACA. Elevated ACA levels were always detected at the sterile bulk stage (i.e., after compounding as 5% or 10% IGIV and filtration with 0.2 μm sterile filters) of all tri-n-butyl phosphate (TNBP)/detergent treated IGIV preparations regardless of process scale. Preparations of ISG with high ACA levels are not suitable for intravenous injection and instead must be administered via other routes, e.g. intramuscular (IM) injection. However, IGIV preparations are more desirable since they are immediately available in the bloodstream and are not subject to loss associated with IM injection. It is thus desirable to have an IGIV product which is both low in ACA and has been subjected to a viral inactivation step.

SUMMARY OF THE INVENTION

The invention is a method for producing an intravenously injectable immune serum globulin (IGIV) preparation with low anticomplement activity which has been chemically treated to render it substantially free of lipid-enveloped viruses. The method comprises a solvent/detergent viral inactivation step followed by an incubation step. We have discovered that the incubation step is necessary to achieve an acceptable level of ACA low enough to allow the ISG to be administered by intravenous injection. The incubation step should be conducted under controlled time, pH, temperature, and ionic strength. Preferably, the pH should be maintained between about 3.5 and about 5.0, the temperature should be within a range of about 2 to about 50° C., and the ionic strength should be less than about 0.001M. In a preferred embodiment the ACA of the ISG preparation decreases gradually over a period of at least about ten days when the ISG is maintained at a pH of about 4.25 at low ionic strength (less than about 0.001M) and the viral inactivation step (in a model system) results in a substantial reduction (i.e. at least 4 logs) in the titer of lipid enveloped viruses.

BRIEF DESCRIPTION OF THE FIGURE

FIG. 1 shows a comparison of the typical average observed ACA levels of 5% IGIV solutions treated according to the SD process and with or without the follow-up incubation of the present invention.

SPECIFIC EMBODIMENTS

Materials and Methods

The starting material for the process of this invention is unmodified human immune serum globulin. In the specification and claims the term "immune serum globulin" is used to define the substance also referred to in the literature variously as gamma globulin, IgG and immunoglobulin G. It consists predominantly and preferably of at least about 85 percent of the 7S species of gamma globulin, which has a molecular weight of about 160,000. Any remainder is preferably 9S species, with a molecular weight of about 300,000. Both standard immune and hyperimmune serum globulins, e.g., tetanus, rabies and hepatitis immune serum globulins, can be employed, the solvent/detergent treated product being immune and hyperimmune ISG, respectively. Thus, a suitable starting material for the process of this invention is Cohn's Fraction II or Fraction III filtrate. (See Refs. 13, 14.)

Fraction II, by ultracentrifugation studies, is predominantly (about 85 percent) the 7S (sedimentation constant of 7) species of gamma globulin with an average molecular weight of 160,000. The remaining protein is essentially 9S material with a M.W. of about 300,000. Wet Fraction II paste (approximately 30 percent solids) is commonly lyophilized to obtain dry ISG powder which is then dissolved and prepared for intramuscular injection as a 16.5 percent sterile solution. Either the wet Fraction II paste or the dry ISG powder is a suitable starting material for the process of this invention.

Gamma globulin obtained by any process which has essentially the same composition of protein components as found in the Cohn Fraction II or Fraction III filtrate can be used as starting material in the present process. Both standard immune serum globulin and hyperimmune serum globulin can be employed as starting materials. As is well known, the latter is produced from plasma or serum obtained from selected donors who have much higher titers for a specific antibody than is normally found in the average population. These donors have either been recently immunized with a particular vaccine or else they have recently recovered from an infection or disease. These high titer sera or plasmas are pooled and subjected to the usual Cohn fractionation procedures up to the point of isolating Fraction II.

Furthermore, because the amount of antibody required to achieve a desired immunological response is substantially less when administered intravenously, it will be apparent the intravenous dose will be substantially less than the intramuscular dose which will produce the same serum antibody titer. Thus, the dose of intramuscular ISG and hyperimmune serum globulin must be higher than that required to achieve the same serum antibody titer when globulin of the same antibody activity is administered intravenously.

The starting wet paste or lyophilized powder is dissolved in a volume of water or other physiologically-acceptable carrier to provide a protein solution of a concentration of about 0.5–20% preferably about 5 to 10 percent. If Fraction III filtrate is employed, the aqueous solution must be concentrated by conventional techniques to the desired protein concentration. Any protein concentration may be used in this method; however, the above range is preferred from a practical standpoint.

After the protein has been dissolved or concentrated, the solution is adjusted to a pH of about 3.5 to 5.0 preferably about 3.8 to 4.2, by addition of a physiologically-acceptable acid such as hydrochloric acid. In general, the pH is adjusted to a point whereat the monomeric material in the protein solution is maintained at a maximum. However, the pH must not be so low as to result in gelation. The temperature should not be harmful to the ISG material. Good results are obtained within the temperature range of about 0–20° C. It is not necessary to hold the so-adjusted material for any period of time prior to the next step; however, the material may be held, if desired, without detrimental effects.

The protein solution at the appropriate pH (preferably 3.8–4.2) may be diafiltered with at least 4 volume exchanges of water to reduce the alcohol concentration from approximately 17% (Filtrate III) to about 2% alcohol. The efficacy of solvent/detergent as a viral inactivation method is much better at or above ambient temperatures; however, high concentrations of alcohol at these temperatures will denature the IgG molecules. Thus, this inactivation must be performed in low alcohol concentration.

Next, the protein concentration of the so-treated material is adjusted to the level desired for incubation with TNBP/detergent, generally less than 10% protein for maximum viral inactivation. This adjustment is accomplished by conventional techniques not detrimental to ISG, e.g., ultrafiltration, reverse osmosis, sublimation, evaporation, etc. Prior to addition of TNBP/detergent, the pH may be adjusted within a wide range, depending on the detergent to be used. With Tween 80, the pH may be as low as 3.5, where the IgG starts becoming unstable. With cholate, the pH is adjusted to within the range of 5.0–6.4, preferably about 5.6, prior to addition of TNBP/detergent. Satisfactory cholate solubility during incubation was achieved by adjusting the immunoglobulin solutions to a pH of 5.5 or higher prior to addition of TNBP and sodium cholate. Adjusting the IgG solution to pH values lower than 5.5 is not suitable because the solubility of sodium cholate is highly dependent on pH (cholic acid pK=6.4), with poor solubility at pH 5.5 or lower. Furthermore, maximum viral inactivation during incubation with TNBP/cholate was observed at pH values less than 6.0 in experiments which employed model viruses spiked into IgG solutions. The inactivation of HIV-1 and BVDV (bovine viral diarrhea virus, which is employed as a model for hepatitis C) was accelerated at pH 5.8, with inactivation to the detection limit occurring in 1–2 hours, whereas inactivation to the detection limit required a minimum of 6 hours when pH 7 conditions were used.

Next, the TNBP/detergent is added to the protein solution (preferably less than 8% [w/w], pH 5.8) mixed thoroughly, and then incubated above ambient temperatures, for example 30° C., with continuous agitation or mixing. Target TNBP/cholate levels for optimal viral inactivation during the incubation step should be >3 mg/mL TNBP and >2 mg/mL cholate as defined by Edwards et al. (8) Moreover, for effective viral inactivation, it is important that the solution is essentially free of particulates in order to facilitate thorough mixing of solvent/detergent and IgG solution. After incubation with TNBP/cholate under these conditions, greater than 5.2 $\log_{10}$ reduction of HIV-1 and greater than 4.0 $\log_{10}$ reduction of BVDV were detected.

After completing the incubation which provides the viral inactivation, the solvent and detergent molecules must be removed in order to achieve a final product with low levels of residual TNBP and cholate which would be suitable for intravenous administration. Generally, procedures to remove detergent are also effective in removing TNBP, and vice versa. Very low levels of TNBP and cholate in the final container can be achieved by a combination of filtration, diafiltration and hydrophobic chromatography. After completing the incubation, the majority of cholate (and TNBP) can be removed from the protein solution by filtration, providing the solution had been previously adjusted to a lower pH value such as 4.0, because sodium cholate is sparingly soluble in aqueous solutions at such pH values. Moreover, all processing steps which follow the solvent/detergent incubation are performed at lower pH values (i.e., 4.0) because IgG molecules are more stable at pH values between 3.5–5.0, in low ionic strength solutions. (2) Thus, after incubation with TNBP/cholate, the protein solution is adjusted to approximately pH 4.0 and incubated at 0–8° C. in order to promote cholate precipitation. Next, filtration is employed to remove the precipitated cholate from the IgG solution.

The so-treated solution is diafiltered with at least four volume exchanges of water to reduce the ionic strength and to remove additional TNBP and cholate. After or during the above treatment, the pH is measured and maintained within the range of about 3.5–5.0. The protein concentration of the so-treated material is adjusted to 10–30%, usually 13% (w/v) by employing conventional techniques not detrimental to ISG, e.g., ultrafiltration, reverse osmosis, sublimation, evaporation, etc. Again the pH of the preparation is maintained within the range of about 3.5–5.0, preferably about 3.8–4.2.

In the present invention, hydrophobic chromatography is employed to remove the TNBP and cholate not eliminated by the filtration and diafiltration steps, and thus provide a final product with low levels of residual TNBP and cholate which is suitable for intravenous administration. Hydrophobic chromatography is a method for TNBP removal from protein solutions that has fewer drawbacks and limitations than other available methods such as oil extraction, ion exchange or affinity chromatography. In part, this is because the protein of interest (IgG) remains in solution throughout the TNBP removal process. Polystyrene-based resins (typically PLRP-S from Polymer Laboratories, Amherst, Mass.) were used to remove the solvent/detergent from solution, as we have found the polystyrene-based resins to be superior to other resins, such as silica-based C-18 resins.

Next, the ISG preparation is adjusted to 5% or 10% protein, and treated to render it tonic, i.e., to render it compatible with physiological conditions, or render it physiologically acceptable upon injection. In a preferred embodiment, the tonicity is adjusted to about 230 to about 490 mosmol/kg solvent. More preferably, the tonicity range is from about 250 to about 350 mosmol/kg solvent, and most preferably the tonicity range is from about 260 to about 325 mosmol/kg solvent. The 5% formulation (5% IGIV) is made tonic by the addition of 10% maltose. The 10% formulation contains 0.2 M glycine in order to achieve an isotonic preparation without large quantities of sugar. The product with either formulation (Gamimune®N 5% or Gamimune®N 10%) experiences shifts in molecular distribution (antibody aggregation) when the ionic strength of the low pH solution is increased. Therefore, sodium chloride, which is often used to achieve tonicity, should not be used.

The so-treated solution is incubated at pH 4.25 under low ionic strength conditions (NLT 21 days at 20–27° C. preferred) in order to provide a lowering of ACA levels. The ionic strength is determined according to Perrin (18), and in a preferred embodiment the ionic strength should be less than about 0.001M. Elevated ACA levels were always detected at this stage of all TNBP/cholate treated IGIV preparations (regardless of process scale); however, ACA levels are gradually lowered by incubation at pH 4.25 under low ionic strength conditions (Tables 3, 5–7). While there is no strict rule for determining when the ACA level is low enough to be an acceptable level suitable for intravenous administration, IGIV preparations should have ACA levels as low as possible.

The Figure depicts the typical average reduction of ACA observed in 5% IGIV solutions following SD treatment. For a 5% ISG formulation the acceptable level suitable for intravenous administration preferably would be less than about 45 $CH_{50}$ units/mL, and more preferably less than about 30 $CH_{50}$ units/mL. For a 10% ISG formulation, the acceptable level suitable for intravenous administration preferably would be less than about 60 $CH_{50}$ units/mL, and more preferably less than about 45 $CH_{50}$ units/mL. As used herein, one unit of ACA activity (one $CH_{50}$ unit) is defined as the amount of protein capable of activating 50% of the complement in an optimally titered complement and red blood cell/hemolysin system. The assay measures the amount of complement that is bound by the mixture of standardized amounts of complement and protein. See refs. 19–20 for a discussion of the assay. Briefly, red blood cells that have been sensitized by preincubation with red blood cell antibodies are added to the complement/protein mixture. In the presence of free complement (not already bound by the protein) these sensitized cells will lyse, releasing hemoglobin which can be quantitated as a measure of the degree of lysis. In parallel, sensitized red blood cells are also added to a buffer control-complement mixture, whose degree of lysis is defined as 100%. The difference between the actual amount of complement needed to give 100% lysis and the amount of complement remaining unbound in the presence of protein equals the amount of complement actually bound by the protein, or anticomplement activity.

Results

Anticomplement Activity of ISG Resulting From Viral Inactivation Process

To establish the effect of the SD viral inactivation process on solutions containing ISG which are formulated according to the Tenold '608 patent, the experiments depicted in Table 1 were performed. The starting material (SM) was Cohn process filtrate III which had been ultrafiltered to about 5% protein and then diafiltered with four volumes of water.

In the control experiment, incubation (−)/SD (−), the SM was not subjected to any incubation or solvent/detergent treatment. In the incubation (+)/SD (−) experiment, the pH of the SM was adjusted to 7.0, the solution was incubated at 30° C. for ten hours, and then the pH was reduced to 4.0. In the incubation (+)/SD, TNBP & Tween 80 (+) experiment, the pH of the SM was adjusted to 7.0, 3 mg/mL TNBP and 2 mg/mL Tween 80 were added to the solution, the solution was incubated at 30° C. for ten hours, and then the pH was reduced to 4.0. In the incubation (+)/SD, TNBP & cholate (+) experiment, the pH of the SM was adjusted to 7.0, 3 mg/mL TNBP and 2 mg/mL cholate were added to the solution, the solution was incubated at 30° C. for ten hours, and then the pH was reduced to 4.0. The solutions in each experiment were then diafiltered with four volumes CWFI (cold water for injection) and concentrated by ultrafiltration. After addition of dry maltose to 10% w/v, the 5% IGIV solution (pH 4.25) was filtered through a 0.2 μm filter.

TABLE 1

Anticomplement activity in 5% IGIV produced by variations of the Solvent/Detergent IGIV Process

| | ACA ($CH_{50}$/mL) |
|---|---|
| Control (no solvent/detergent treatment, no 30° C. incubation) | 25 |
| Incubate at 30° C. for 10 hr (no solvent/detergent) | 22 |
| Incubate at 30° C. for 10 hr NLT 3 mg/mL TNBP NLT 2 mg/mL Tween 80 | 68 |
| Incubate at 30° C. for 10 hr NLT 3 mg/mL TNBP NLT 2 mg/mL cholate | >100 |

*These samples were assayed for ACA after final compounding according to the Tenold '608 patent, but they were not incubated at pH 4.25 and 22° C. prior to analysis.

The results listed in Table 1 show that levels of ACA increased in IgG samples after incubation with TNBP/cholate or TNBP/Tween 80. ACA levels were not elevated in IgG samples that were incubated for 10 hr at 30° C. in the absence of solvent/detergent. These results suggest that ACA levels of IGIV samples were not elevated by either processing manipulations or incubation for 10 hr at 30° C. in the absence of solvent/detergent.

TABLE 2

Anticomplement activity in 5% IGIV spiked with TNBP/Na cholate

| | ACA ($CH_{50}$/mL) |
|---|---|
| 5% IGIV, no TNBP/cholate | 12 |
| 5% IGIV with 100 µg/mL TNBP, 100 µg/mL Na cholate | 13 |

Furthermore, spiking experiments (with TNBP and Na cholate, Table 2) have demonstrated that the elevated anticomplement activity levels were not artifacts caused by carrying out the anticomplement assay in the presence of trace levels of TNBP/Na cholate. Thus, using the prior art SD process for viral inactivation of a solution containing ISG, subsequently formulated according to the Tenold '608 patent, yields a product which has high ACA and is unsuitable for intravenous administration. In a similar experiment, SD treated samples which were not incubated (Table 3, Initial Testing) had ACA levels greater than 100 units.

TABLE 3

Reduction in Anticomplement activity of samples previously treated with TNBP/cholate

| | ACA ($CH_{50}$/mL) | |
|---|---|---|
| Sample | Initial Testing (no incubation) | After incubation 6 wk. @ 5° C. 3 wk. @ 22° C. |
| RB21872-16 | >100 | 33 |
| RB21872-17 | >100 | 34 |
| RB21872-18 | >100 | 36 |
| RB21872-20 | >100 | 27 |

However, when duplicate SD treated samples were incubated for extended periods of time (6 weeks at 5° C. and 3 weeks at 22° C.), the level of ACA was markedly reduced (Table 3, after incubation). This led to further investigation of this surprising observation.

Aggregate Content of ISG Exposed to TNBP/cholate

The samples of the previous experiment (Table 3, Initial Testing) were analyzed by size exclusion (gel permeation) HPLC immediately after compounding to determine the extent of aggregation of the IGIV at the initial time point. HPLC analysis shows nearly complete monomer content in the samples. (Table 4).

TABLE 4

HPLC analysis of non-incubated 5% IGIV samples (Table 3 Initial)

| Sample | Aggregate (%) | Dimer (%) | Monomer (%) | Fragment (%) |
|---|---|---|---|---|
| RB21872-16, initial | 0.140 | 0.00 | 99.86 | 0.00 |
| RB21872-17, initial | 0.146 | 0.00 | 99.85 | 0.00 |
| RB21872-18, initial | 0.124 | 0.00 | 99.88 | 0.00 |
| RB21872-20, initial | 0.172 | 0.00 | 99.83 | 0.00 |

Previously, high IgG aggregate levels were shown to correlate with high anticomplement activity. However, results from analysis of the samples show the level of ACA in the samples to be greater than 100 units. (Table 3, 'Initial Testing') The HPLC analysis shows that the high ACA following the TNBP/cholate treatment was not due to the presence of aggregated IgG molecules.

Varied Conditions of Time and Temperature

The SM was the same as in the previous experiment, and experimental conditions were similar with the following changes. The solutions were treated with TNBP/cholate at pH 7.0 and then were compounded to 5% IGIV, 10% maltose, pH 4.25, as above. The ACA was assayed immediately after final compounding, after a first incubation for nine days at 5° C., and after a second incubation for 21 days at either 22° C. or 5° C. The results are presented in Table 5.

TABLE 5

ACA of TNBP/cholate treated IGIV samples

| Sample Point | ACA ($CH_{50}$/mL) |
|---|---|
| Intermediate Samples | |
| Initial sterile bulk | >100 |
| Incubated 9 d. @ 5° C. | >100 |
| Final Incubation | |
| 21 d. @ 22° C. | 49 |
| 21 d. @ 5° C. | 71 |

In the initial sterile bulk sample, which was treated with TNBP/cholate at pH 7.0, the level of ACA was again greater than 100 units for the initial time point, confirming the observations noted in Table 3. Upon incubation at 5° C. for nine days, the ACA remained greater than 100 units. The final incubation step at either 5° C. or 22° C. shows that the reduction in ACA is dependent on temperature, with faster reduction in ACA observed at higher temperatures.

Effect of pH During Solvent/detergent Treatment on ACA

ACA levels were evaluated after incubation with TNBP/cholate at pH 5.8 because better viricidal activity was observed at pH values less than 6.0. Generally, the non-incubated sterile bulk samples of material incubated at pH 5.8 had lower ACA levels than the pH 7.0 samples, but the trend of lowering ACA upon incubation was repeated in the pH 5.8 samples. In fact, the ACA levels continue to decrease beyond the 21 day incubation in samples that initially had elevated ACA levels after incubation with TNBP/cholate at pH 5.8 (Table 6). As was previously noted for the samples incubated at pH 7.0, the lowering of ACA was not due to decreasing levels of aggregated IgG molecules because the material treated at pH 5.8 was essentially monomeric IgG prior to 22° C. incubation (HPLC analysis, sample A4, Table 8).

TABLE 6

Sample A4 - ACA upon extended incubation

| Incubation at 22° C. (days) | $CH_{50}$/mL |
|---|---|
| 0 | 122 |
| 10 | 73 |
| 19 | 55 |
| 25 | 56 |
| 28 | 45 |
| 30 | 40 |
| 34 | 39 |
| 41 | 33 |

TABLE 6-continued

Sample A4 - ACA upon extended incubation

| Incubation at 22° C. (days) | $CH_{50}/mL$ |
|---|---|
| 48 | 30 |
| 55 | 29 |

Similar results were achieved with samples formulated to 10% IGIV, 0.2 M glycine in the sterile bulk stage. Upon incubation at low ionic strength at pH 4.25 for 10 and 21 days, the levels of ACA were seen to decline in both 5% IGIV samples and 10% IGIV samples. (Table 7) The decrease in ACA can thus be observed over a range of ISG concentrations and over a range of pH values for the solvent/detergent treatment. (Tables 3, 5, 7) HPLC analysis (Table 8) of the sterile bulk samples presented in Table 7 confirmed that the elevated ACA levels were not due to aggregation of ISG molecules.

TABLE 7

ACA of samples treated with TNBP/cholate at pH 5.8

| Sample | Sterile bulk (day zero) ($CH_{50}/mL$) | 10 days incubation at 20–27° C. ($CH_{50}/mL$) | 21 days incubation at 20–27° C. ($CH_{50}/mL$) |
|---|---|---|---|
| A1 (5% IGIV) | 43 | ND | 10 |
| A2 (5% IGIV) | 31 | 14 | 15 |
| A3 (5% IGIV) | 44 | 15 | 12 |
| A4 (5% IGIV) | 122 | 73 | 55 |
| B1 (10% IGIV) | >100 | 48 | 46 |
| B2 (10% IGIV) | 49 | 36 | 30 |
| B3 (10% IGIV) | 53 | ND | 37 |

Taken together, the above results suggest that ISG products which have been subjected to a solvent/detergent viral inactivation process resulting in an undesirable ACA increase can be made suitable for IV administration by incorporating an additional incubation step under the conditions described here to reduce the ACA to an acceptable level.

TABLE 8

HPLC Analysis of sterile bulk samples treated with TNBP/cholate at pH 5.8

| Sample | Aggregate (%) | Dimer (%) | Monomer (%) | Fragment (%) |
|---|---|---|---|---|
| A2 | 0.140 | 0.00 | 99.86 | 0.00 |
| A3 | 0.146 | 0.00 | 99.85 | 0.00 |
| A4 | 0.124 | 0.00 | 99.88 | 0.00 |

CONCLUSION

The ACA increase resulting from the solvent/detergent treatment of the IGIV (antibody) solution appears to be an unavoidable secondary effect of TNBP/detergent treatment to inactivate viruses in the solution. I have discovered that by incubating the solution of IGIV at low pH (4.25) and low ionic strength (0.001M) for a relatively long period of time (at least about 10 days), the ACA gradually decreases over the period of incubation.

The prior art discloses a method of producing IGIV (the Tenold '608 patent) using low pH and low ionic strength. The Tenold '608 method omits the viral inactivation step, and thus avoids the problem of increased ACA, but the possibility of viral activity remains. Unlike Tenold, incubation is an essential aspect of the present invention for reducing the ACA.

The Neurath et al. '573 patent teaches the solvent/detergent viral inactivation step. However, Neurath '573 does not mention controlling the pH and also does not mention any consequences of the process relating to ACA. Elevated ACA levels were detected at the sterile bulk stage of TNBP/cholate treated IGIV preparations. However, ACA levels decreased upon incubation for at least about 10 days at pH 4.25, low ionic strength, and not less than about 20° C. (See Tables 5–7) The prior art describes several approaches to lowering ACA levels of purified IgG preparations, including removal of IgG aggregates. (11) IgG aggregates have been shown to activate the complement system in vivo. (1) In the present invention, however, lowering of IgG ACA was not due to decreasing levels of IgG aggregates because these TNBP/cholate treated IGIV preparations contained low levels of aggregated IgG (as measured by HPLC, Tables 4, 8) prior to incubation under such conditions.

It would be desirable to produce substantially virus-free IGIV, but following the prior art results in a product with an unacceptable level of ACA. Note that Tenold '608 states that the product is substantially free of ACA, but use of the SD process in conjunction with Tenold '608 does result in high levels of ACA: experimental results reported here show that treating ISG solutions with the SD process and then formulation according to the Tenold '608 patent leads to a product with high ACA. (See Tables 1, 3, 5–7) The surprising finding reported here is that a follow-up (terminal) incubation step lowers the ACA of the solvent/detergent treated solution. The typical average observed ACA levels of 5% IGIV solutions treated according to the SD process and with or without the follow-up incubation are compared in the Figure. The present invention thus includes a previously unobserved method of reducing the ACA by incubating under controlled conditions of pH, temperature, and ionic strength for a period of time, thus allowing the product to be administered by intravenous injection.

Mitra '714 does not suggest the use of a S/D process but, instead, reports that a relatively brief incubation of an ISG product under similar conditions results in a substantially virus free preparation. (10) However, employing incubation under such conditions to provide a lowering of anticomplement activity is a novel application of these incubation conditions which were previously employed in the IGIV process for inactivation of enveloped viruses.

The newly developed IGIV process reported here, which includes an additional internationally accepted viral inactivation procedure (treatment with TNBP/cholate), generates IgG preparations which have low ACA levels and are suitable for IV administration. The major advantage is that an IGIV product with improved safety can be obtained by a two-step process that includes a TNBP/cholate treatment for viral inactivation and incubation under conditions that afford low ACA levels that are suitable for IV administration.

The above disclosure is intended to illustrate the invention, and it is thought variations will occur to those skilled in the art. Accordingly, it is intended that the scope of the invention should be limited only by the claims below.

REFERENCES

1 Barandun, S. et al., *Vox Sang.* 7: 157–174 (1962).
2 Tenold, R. A., U.S. Pat. No. 4,396,608 (Aug. 2, 1983).

3 Fernandes, P. M. et al., U.S. Pat. No. 4,186,192 (Jan. 29, 1980).

4 Malgras, J. et al., *Rev. Franc. Trans.* 13: 173 (1970).

5 Sgouris, J. T., *Vox Sang.* 13: 71 (1967).

6 Pappenhagen, A. R. et al., U.S. Pat. No. 3,903,262 (Sep. 2, 1975).

7 Neurath, A. R. and Horowitz, B., U.S. Pat. No. 4,540,573 (Sep. 10, 1985).

8 Edwards, C. A. et al., *Vox Sang.* 52: 53–59 (1987).

9 Louie, R. E. et al., *Biologicals* 22: 13–19 (1994).

10 Mitra, G. and Mozen, M., U.S. Pat. No. 4,762,714 (Aug. 9, 1988).

11 Polson, A. and Ruiz-Bravo, C., *Vox Sang.* 23: 107–118 (1972).

12 Seng, R. L. and Lundblad, J. L., U.S. Pat. No. 4,939,176 (Jul. 3, 1990)

13 Cohn et al., *J. Am. Chem. Soc.* 68: 459 (1946).

14 Oncley et al., *J. Am. Chem. Soc.* 71: 541 (1949).

15 Kameyama, S. et al., U.S. Pat. No. 5,151,499 (Sep. 29, 1992).

16 Uemura, Y. et al., *Vox Sang.* 67: 246–254 (1994).

17 Yang, Y. H. J. et al., *Vox Sang.* 67: 337–344 (1994).

18 Perrin, D. D. and Dempsy, B., Buffers for pH and Metal Ion Control (Chapman and Hall, London, 1974), pp. 6–7.

19 Palmer, D. F. and Whaley, S. D., *Complement Fixation Test*, in Manual of Clinical Laboratory Immunology (Ed. N. R. Rose, et al., American Society for Microbiology, Washington, D.C., 1986) pp. 57–66.

20 Mayer, M. M., *Quantitative C'Fixation Analysis, Complement and Complement Fixation*, in Experimental Immunochemistry (Ed. E. A. Kabat and M. M. Meyer, Thomas, Springfield, Ill., 1961), pp. 214–216, 227–228.

What is claimed is:

1. A method of treating a solution of antibodies which may have virus activity, the method comprising a) contacting the solution with a trialkylphosphate and a detergent under conditions sufficient to substantially reduce any virus activity and resulting in an increased level of anticomplement activity; and b) then incubating the solution of step a) under conditions of controlled time, pH, temperature, and ionic strength, such that the increased anticomplement activity of the solution is reduced to an acceptable level suitable for intravenous administration.

2. The method of claim 1, wherein the anticomplement activity is reduced to less than about 60 $CH_{50}$ units/mL.

3. The method of claim 1, wherein the solution comprises about 5% wt./wt. antibody and the anticomplement activity is less than about 45 $CH_{50}$ units/mL.

4. The method of claim 3, wherein the solution comprises about 5% wt./wt. antibody and the anticomplement activity is less than about 30 $CH_{50}$ units/mL.

5. The method of claim 1, wherein the solution comprises about 10% wt./wt. antibody and the anticomplement activity is less than about 60 $CH_{50}$ units/mL.

6. The method of claim 5, wherein the solution comprises about 10% wt./wt. antibody and the anticomplement activity is less than about 45 $CH_{50}$ units/mL.

7. The method of claim 1, wherein the incubation is for at least about ten days.

8. The method of claim 1, wherein the pH is maintained within a range of about 3.5 to about 5.0.

9. The method of claim 1, wherein the temperature is maintained within a range of 2° C. to 50° C.

10. The method of claim 1, wherein the ionic strength is less than about 0.001 M.

11. The method of claim 1, wherein at least about 99% of the antibodies are monomeric.

12. The method of claim 1, comprising the further step of adjusting the tonicity of the solution to a physiologic value under such conditions that the ionic strength is not appreciably altered.

13. The method of claim 12, wherein the tonicity of the solution is adjusted by adding a carbohydrate to the solution.

14. The method of claim 13, wherein the carbohydrate used is maltose.

15. The method of claim 12, wherein the tonicity of the solution is adjusted to a range of about 230 to about 490 mosmol/kg solvent.

16. The method of claim 15, wherein the tonicity of the solution is adjusted to a range of about 274 to about 309 mosmol/kg solvent.

17. The method of claim 12, wherein the tonicity of the solution is adjusted by adding an amino acid to the solution.

18. The method of claim 17, wherein the amino acid used is glycine.

19. The method of claim 1, wherein the trialkylphosphate is tri-n-butyl phosphate and the detergent is selected from polysorbate 80 and sodium cholate.

20. The method of claim 1, wherein the solution has a pH between about 3.5 and about 6.0 during step a).

21. An intravenously injectable immune serum globulin preparation produced by the method of claim 1 and substantially free of lipid enveloped viruses, wherein the preparation has an ionic strength less than about 0.001 M, a pH between about 3.5 and about 5.0, an antibody concentration of about 5% wt./wt., and a maltose concentration of about 10% wt./wt.

22. The preparation of claim 21, wherein the pH is about 4.25.

23. An intravenously injectable immune serum globulin preparation produced by the method of claim 1 and substantially free of lipid enveloped viruses, wherein the preparation has an ionic strength less than about 0.001, a pH between about 3.5 and about 5.0, an antibody concentration of about 10% wt./wt., and a glycine concentration of about 0.2 M.

24. The preparation of claim 23, wherein the pH is about 4.25.

* * * * *